(12) United States Patent
Bittar

(10) Patent No.: US 7,789,842 B2
(45) Date of Patent: Sep. 7, 2010

(54) ADJUSTABLE ARM SLING

(76) Inventor: Donald Bittar, 3101 N. Riverside, Indialantic, FL (US) 32903

( * ) Notice: Subject to any disclaimer, the term of this patent is extended or adjusted under 35 U.S.C. 154(b) by 146 days.

(21) Appl. No.: 11/906,295

(22) Filed: Oct. 1, 2007

(65) Prior Publication Data
US 2009/0088673 A1    Apr. 2, 2009

(51) Int. Cl.
A61F 5/00    (2006.01)
A61F 5/02    (2006.01)

(52) U.S. Cl. .................................. 602/4; 2/44; 2/45
(58) Field of Classification Search .................. 602/4, 602/5, 19, 20; 128/875, DIG. 19; 2/44, 45
See application file for complete search history.

(56) References Cited
U.S. PATENT DOCUMENTS
2,111,963 A  *  3/1938  Coombs ...................... 602/4
2,796,862 A  *  6/1957  Borntraeger ................. 602/4
4,480,637 A  *  11/1984 Florek ........................ 602/4
5,141,488 A  *  8/1992  Schrader ..................... 602/4
5,413,552 A  *  5/1995  Iwuala ........................ 602/4

* cited by examiner

Primary Examiner—Patricia Bianco
Assistant Examiner—Tarla R Patel
(74) Attorney, Agent, or Firm—Roger M. Rathbun

(57) ABSTRACT

An adjustable sling that can be used to hold a patient's arm, wrist and hand in a multiple positions and eliminate stress to the neck and shoulder. The adjustable sling has a pouch for holding the patient's arm, wrist and hand and the pouch is held at its opposite ends by a pair of straps that are detachably affixed to the pouch. The straps pass over the shoulders of the patient on both sides of the head with free ends extending downwardly over the back of the patient to be affixed to the clothing of the patient much in the manner of suspenders. Both of the straps have length-adjusting devices that allow the length of the straps to be adjusted in accordance with the desired position and angle of the pouch. The free ends may be attached to the belt of the patient at the patient's back with connecting devices that clamp onto the belt.

14 Claims, 4 Drawing Sheets

ADJUSTABLE ARM SLING

FIELD OF THE INVENTION

The present invention relates to a sling for retaining the arm of a patient in a relatively fixed location and, more particularly, to a sling that has enhanced adjustability to readily enable the patient to place the arm in any one of numerous secure positions and eliminate strain to the neck and shoulder from the weight of the arm.

BACKGROUND OF THE INVENTION

It is a common practice in the care of patients, particularly after a fracture of an arm bone of a patient, to position the patient's arm in a relatively fixed position during the healing. In such cases, it is normal to have the arm immobilized by use of a sling that is supported by the patient and which holds the arm in the desired position. The arm must be held securely by the sling, however, depending on the particular fracture, the arm may be retained in various positions, that is, the arm may be held in the sling with the wrist elevated above the elbow or, alternatively, the wrist may be in some other position, such as level with the elbow or even lower than the elbow.

The arm and associated cast are required to be immobilized for an extended period of time. A sling places excessive weight, for extended periods of time, from the dead weight of the arm and associated cast, on neck and shoulder muscles because of the strap of the sling is draped about the back of the neck. The shoulder and neck muscles are stressed, strained and impaired by the sling and weight of the arm. Often, the neck and shoulder require rehabilitation after the arm no longer requires a sling.

It would therefore be advantageous to have a sling that provides good adjustability and versatility in allowing the user or physician to place the arm in any of a wide variety of positions and yet retain the arm securely in that desired position while also eliminating stress and stain to the neck and shoulder muscles.

SUMMARY OF THE INVENTION

Accordingly, the present invention relates to an adjustable arm sling having enhanced ability to place the arm in a wide variety of positions and yet hold the arm securely in the selected position.

As such, with the present invention, there is a sling that includes a pouch that holds the arm of the patient in a secure, comfortable manner. The pouch has a wrist end that is proximate to the wrist of the patient and an elbow end that is located proximate to the elbow of the patient when the patient's arm is retained within the pouch.

In order to achieve the enhanced adjustability of the sling, the sling includes a first strap that is affixed to the pouch at or approximate to the wrist end and a second strap that is affixed to the pouch at or proximate to the elbow end of the pouch. That attachment can be by means of some easily attachable and detachable system or device such as a hook and loop, button and button-hook, or affixation system sold under the trademark Velcro, however, other means can be utilized to make the attaching and detaching of the straps to the pouch relatively easy for the patient. As will become clear, the use of some attaching and detaching means to affix the straps to the pouch at the front of the patent allows the user the added convenience of being able to put the sling on and to remove the sling with the use of only one hand and which is an advantageous feature of the present invention.

The straps themselves are similar to "suspenders" type of straps and which each pass over a shoulder of the patient on both sides of the patient's head and thereafter pass along the back of the patient where the free ends, that is, the ends not attachable to the pouch, are adapted to be affixed to some part of the patient's clothing. In one exemplary embodiment, there are connecting devices provided at the free ends of the straps similar, again, to the normal connecting devices commonly used with suspenders and the connecting devices can be readily attached to the belt of the patient.

The suspenders type of connecting devices are well known and clamp over clothing or, in the exemplary embodiment, to the belt of the patient at the back of that patient. Other types of connecting devices can, of course, be used to secure the free ends of the straps to clothing of the patient and such other connecting devices may include loops at the free ends of the straps that are adapted to encircle and be thereby held to buttons on the trousers of the patient, again in the fashion of suspenders.

Both the first and second straps have length-adjusting devices to enable the user to adjust the length of the straps and thereby adjust the position and orientation of the pouch at the front of the patient. In an exemplary embodiment, the length adjusting devices are located both at the front of the patient along the strap as well as at the back of the patient so that the length of the straps can be adjusted both at the front and at the back of the patient. Again, the length adjusting devices can be conventional devices normally present on suspenders and which allow the length of the strap to be adjusted.

Along the back of the patient there can also be a junction brace that connect the first and second straps at about the center of the patient's back such the an X is formed by the straps as the pas down the patient's back. The use of the junction brace also stabilizes the straps and makes the straps easier to manipulate in putting on and removing the sling from the patient.

Thus, by the individual length adjusting devices of the straps, the pouch can be located at any one of a number of positions at the front of the patient and the arm held in a variety of orientations, that is, the length adjustments allows the user to place, for example, the arm with the wrist elevated, with the elbow elevated and at various vertical locations along the front of the patient.

As a further feature of the present invention, there can be front and rear braces to provide additional stabilization to the arm while retained within the pouch. There can be a front brace that is located at or proximate to the wrist end of the pouch and a rear brace that is located at or proximate to the elbow end of the pouch. In both cases, the braces can be easily attached and detached from the pouch and, again, the attaching and detaching means may be by a VELCRO hook and loop fastening system, or other system or device. A valuable feature of this invention is the ability of the person wearing the sling to attach and detach the braces from the pouch with a non-dominant hand.

As another significant feature of the present invention, the braces evenly distribute the weight of the arm between both shoulders by-passing the neck. The weight on the neck is completely eliminated. The weight of the arm is also supported by the back brace attached to the clothing. In by-passing the neck, distributing the weight of the arm to both shoulders and supporting the weight of the arm by affixing the brace to the patients clothing all strain and stress to the neck and shoulder is eliminated.

These and other features and advantages of the present invention will become more readily apparent during the following detailed description taken in conjunction with the drawings herein.

DETAILED DESCRIPTION OF THE INVENTION

Figure 1:
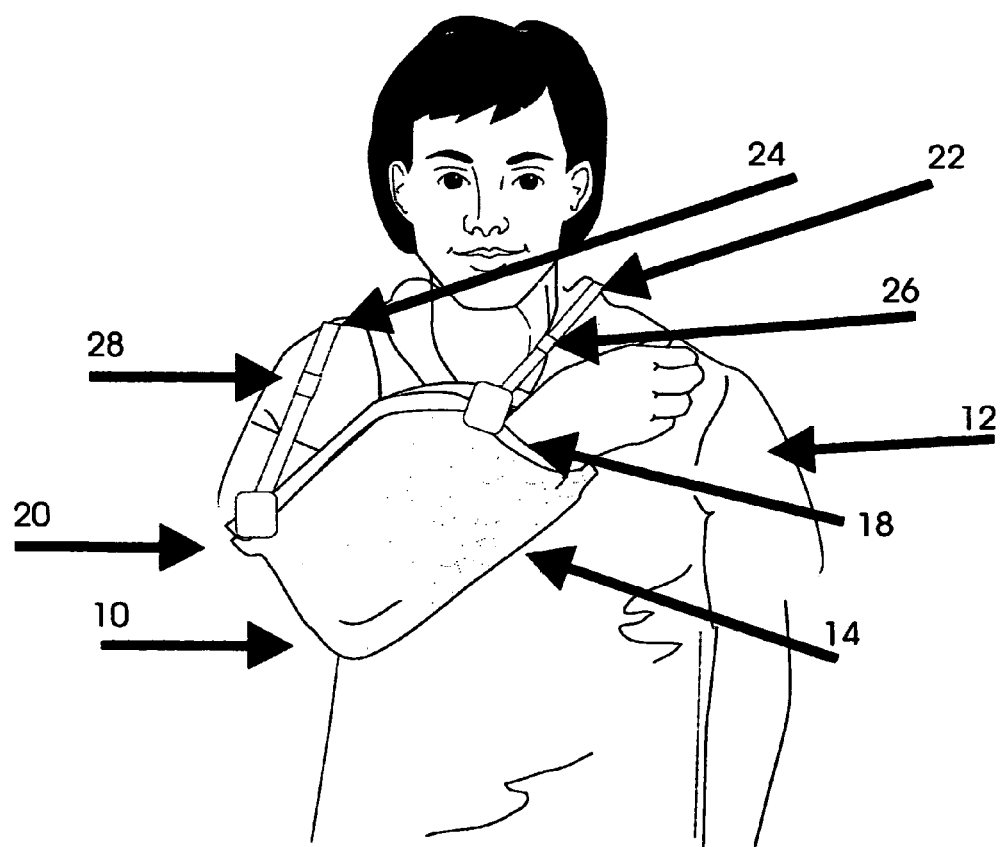
FIG. 1 is a schematic view of the sling of the present invention at the front of a patient.

Referring now to FIG. 1, there is shown a schematic view of the adjustable arm sling 10 constructed in accordance with the present invention. As can be seen, the adjustable arm sling 10 is being worn by a patient 12 and is located at the front of that patient. The adjustable arm sling 10 includes a pouch 14 that contains the arm, wrist and hand and holds it securely. The pouch 14 can be of a conventional design and is normally comprised of a heavy cloth that enwraps the patient's arm to hold it in a comfortable manner. In the orientation as shown in FIG. 1, the pouch 14 has a wrist end 18 and an elbow end 20 depicting the portions of the pouch 14 that are located at or proximate to, respectively, the wrist and elbow of the patient when the patient's arm is held by the pouch 14.

The pouch 14 is retained in its particular orientation by mean of two straps, a first strap 22 and a second strap 24. The first strap 22 is shown to be affixed to the wrist end 18 of the pouch 14 whereas the second strap 24 is shown to be affixed to the elbow end 20 of the pouch 14. In both cases, the means of attaching the first and second straps, 22, 24 is by the use of some easily attachable and detachable device or system. One such system can be a hook and loop fastening system sold under the trademark Velcro however, other devices can be used such as snaps, buttons or the like, it being advantageous in the use of the present invention that the means of attaching and detaching of the first and second straps 22, 24 to the pouch 14 be easy to facilitate so that the adjusting arm sling 10 can be put on and removed by the use of only one hand of the patient, particularly the non-dominate hand.

There are also length adjusting devices 26, 28 included in the adjustable an sling 10 that can be used to change or adjust the length of the first and second straps 22, 24 and such length adjusting devices 26, 28 are conventional and can be the same or similar to those normally provided on suspenders. Thus, as is now seen, by adjusting the length of the first and second straps 22, 24 the location and orientation of the pouch 14 can be adjusted as desired by the patient or caregiver, that is, the pouch 14 can be oriented in the wrist up position, the elbow up position and any position therebetween as well as the vertical height can be selected to provide the support and comfort to the patient's arm.

Figure 2:
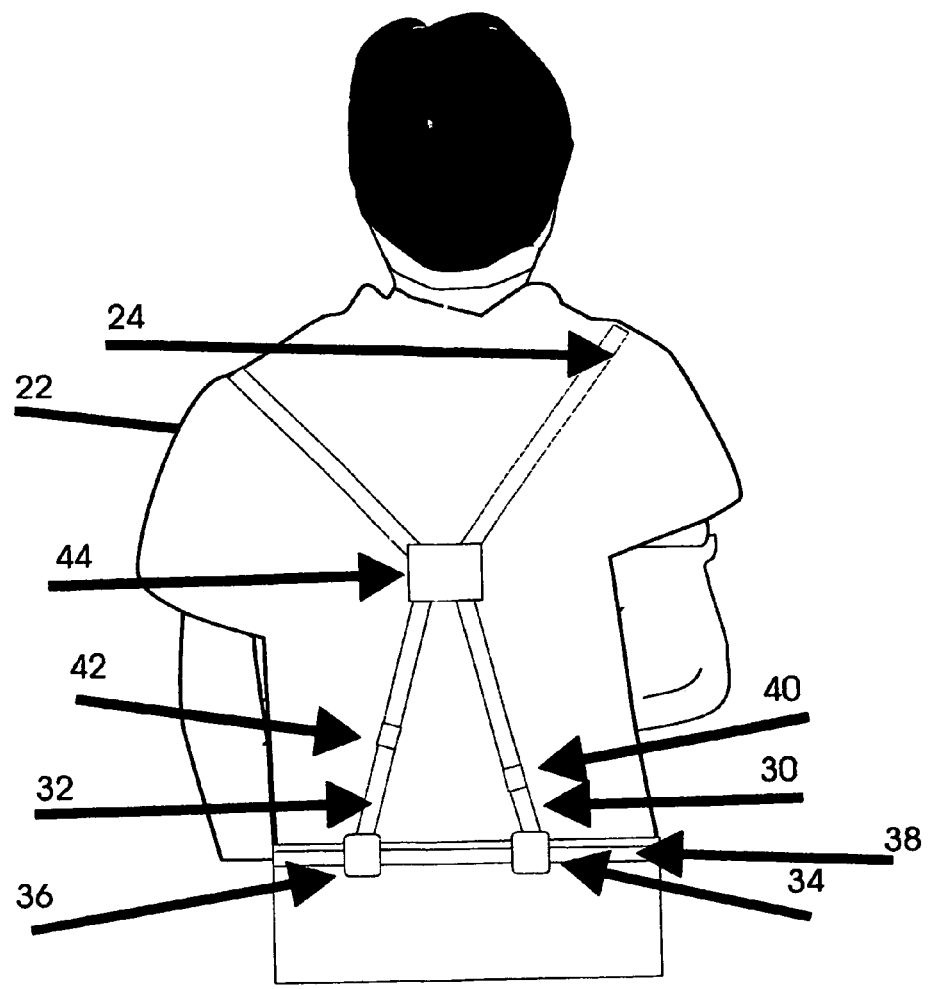
FIG. 2 is a schematic view of the sling of the present invention along the back of a patient.

Turning now to FIG. 2, there is shown a schematic view of the present adjustable arm sling 10 as seen from the back of the patient. Accordingly, the first and second straps 22, 24 pass over the shoulders of the patient on each side of the head and down the back of that patient. The free ends 30, 32 of the first and second straps 22, 24 are provided with connecting devices 34, 36 in order to affix those free ends 30, 32 to some part of the clothing of the patient. In the exemplary embodiment, the free ends 30, 32 are affixed to the belt 38 of the patient along the back of that patient.

The actual connecting devices 34, 36 may vary, however one type of connecting device that is suitable for use with the present invention is the clamp type of device conventionally used with suspenders where the edge of the belt is inserted in between two teethed members and the device is clamped inwardly such that the belt is firmly held between the teeth of those members. Alternate connecting members, however could be used including a loop formed at the free ends 30, 32 of the first and second straps 22, 24 that encircle buttons on the trousers of the patient, again a system conventionally used with suspenders.

There can also be seen in FIG. 2, length adjusting devices 40, 42 provided along the first and second straps 22, 24 respectively, so that the length of the first and second straps 22, 24 can be adjusted at the back of the patient, as well as at the front of the patient, as described with respect to FIG. 1

As also shown on FIG. 2, there is a junction brace 44 that connects the first and second straps 22, 24 at the back of the patient, and which forms an X configuration in the straps across the back of the patient. The junction brace 44 is generally located at or near the center of the patient's back and provides stability to the first and second straps.

Figure 3:
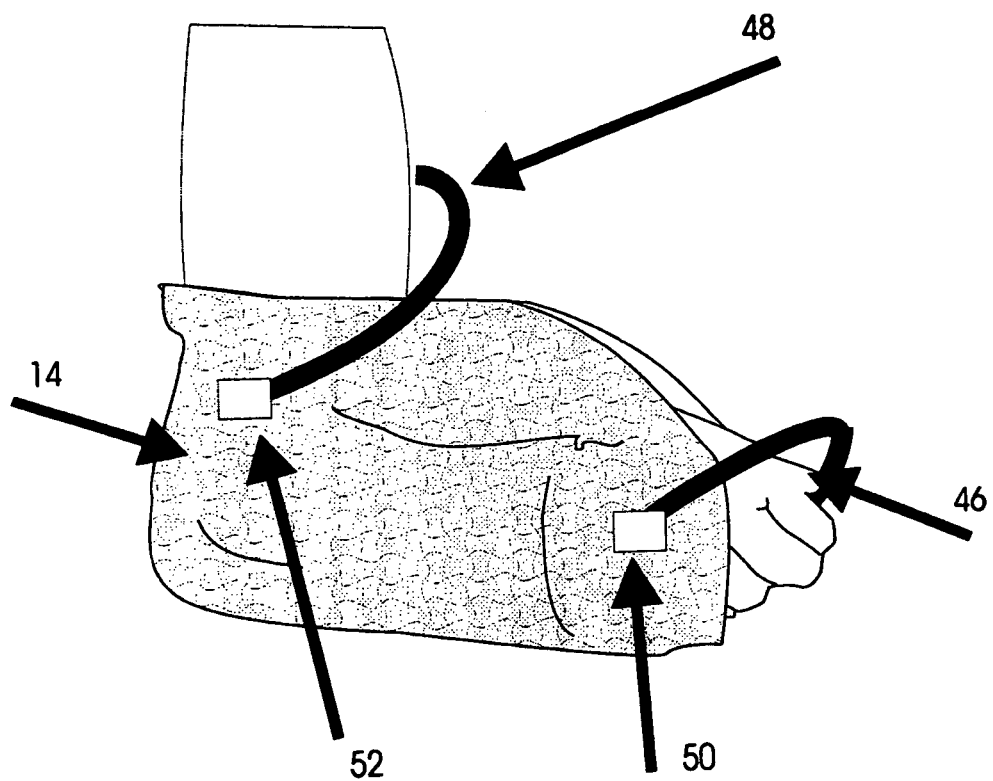
FIG. 3 is a schematic view of the pouch of the present invention and illustrating the front and rear braces used with the pouch of FIG. 1.

Turning next to FIG. 3, there is shown a schematic view of the pouch 14 of the present invention and showing braces, that is, there is a front brace 46 that is located at or proximate to the wrist end 18 and a rear brace 48 that is located at or proximate to the elbow end 20 of the pouch 14. At the ends of the front and rear braces 46, 48 there are fastening devices 50, 52 (only one of the fastening devices on each of the braces is shown in FIG. 3). Again the fastening devices can be a hook and loop fastening system and which allows the user to adjust the length of the front and rear braces 46, 48 to retain the wrist end 18 and the elbow end 20 of the pouch 14 together and better secure the arm within that pouch 14.

Figure 4:
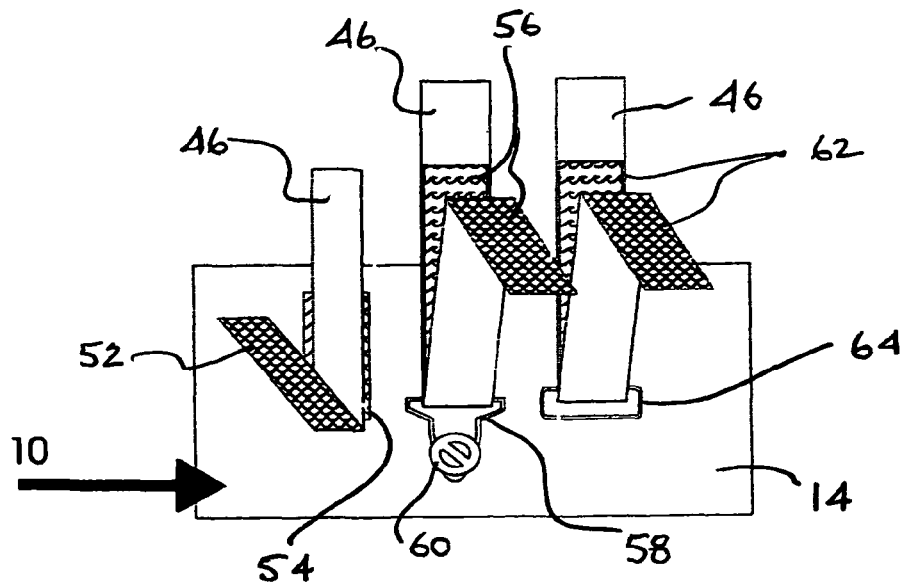
FIG. 4 is a schematic view illustrating typical connecting devices that are usable with the present invention.

Turning now to FIG. 4, taken along with FIG. 3, there is shown various schematic views illustrating typical fastening devices that are usable with the present invention to affix the front and rear braces 46, 48 to the pouch 14. In FIG. 4, only the front brace 46 is illustrated, it being seen that the rear brace 48 has the same means of fastening. As can be seen, the front brace 46 has a loop and hook fastening system 52 that attaches the front brace 46 to a hook and loop fastening system 54 located on the pouch 14. As an alternate, the front brace 46 may have a two sided hook and loop fastening system 56 at its end and which loops through a fastener 58 to attach to a button 60 on the pouch 14. Next, the front brace may have a two sided hook and loop fastening system 62 and passes through an elongated opening 64 in the pouch 14. As can be seen, any of these, or other connecting device can be used to affix the front and rear braces 46, 48 to the pouch 14.

Figure 5:
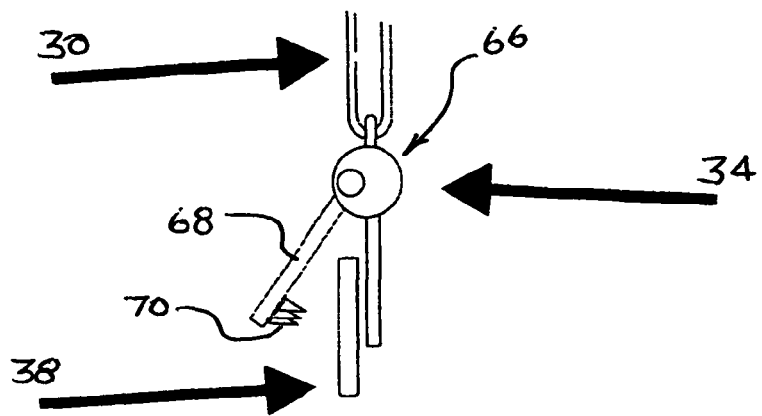
FIG. 5 is a schematic view of a fastening device usable with the present invention.

Finally, turning to FIG. 5, taken along with FIG. 2, there is show a schematic view of a typical connecting device that can be used to affix the free ends 30, 32 of the first and second straps 22, 24 to the belt 38. Again, only the connecting device 34 is illustrated since both connecting devices 34 and 36 can be the same. As such, the free end 30 has a clamp device 66 affixed thereto and which has a moving arm 68 with a sharp projection 70 that can be pivoted to press against and be held to the belt 38.

Those skilled in the art will readily recognize numerous adaptations and modifications which can be made to the adjustable arm sling of the present invention which will result in an improved arm sling, yet all of which will fall within the scope and spirit of the present invention as defined in the following claims. Accordingly, the invention is to be limited only by the following claims and their equivalents.

What is claimed is:

1. An adjustable arm sling for supporting an arm of a patient, the adjustable arm sling comprising a pouch for holding a patient's arm in a wrist up position, the adjustable arm sling having an elbow end for holding the elbow of a patient and a wrist end for holding the wrist of a patient, the pouch configured to be located at the front of a person, a first strap affixed to the wrist end of the pouch to pass over a shoulder and down the back of a patient and having a free end with a connecting device for affixing the free end of the first strap to the clothing of a patient and a second strap affixed to the elbow end of the pouch to pass over the other shoulder and down the back of a patient and having a free end with a connecting device for affixing the free end of the second strap to the clothing of a patient, each of the first and second straps having at least one length adjusting device located between the pouch and the shoulders of a patient to change the length of the first and second straps to selectively and individually adjust the relative locations of the elbow end and the wrist end of the pouch to a wrist up position, the adjustable arm sling further including a front brace having opposed ends affixed to the pouch and extending across a hand of a patient for retaining the hand securely within the pouch and an rear brace having opposed ends affixed to the pouch and extending across the arm for retaining the elbow securely within the pouch.

2. The adjustable arm sling of claim 1 wherein the free ends of the first and second straps are adapted to be affixed to the clothing of a patient at or proximate to the waist of a patient.

3. The adjustable arm sling of claim 1 wherein the first and second straps have connecting devices adapted to be affixed to the clothing of a patient at the back of a patient.

4. The adjustable arm sling of claim 3 wherein the connecting devices are suspenders type clamps adapted to be affixed to a belt of a patient.

5. The adjustable arm sling of claim 3 wherein the connecting devices are loops adapted to fit over buttons on clothing of a patient.

6. The adjustable arm sling of claim 1 wherein the adjustable arm sling further includes at least one length adjusting device on each of the first and second straps located at the back of a patient to adjust the length of the straps.

7. The adjustable arm sling of claim 1 wherein the adjustable arm sling includes at least two length adjusting device on each of the first and second straps with one of the length adjusting devices located at the front of a patient and the other located at the back of a patient.

8. The adjustable arm sling of claim 1 wherein the strap affixed to the wrist end of the pouch is affixed by a hook and loop fastening system.

9. The adjustable arm sling of claim 1 wherein the strap affixed to the elbow wrist end of the pouch is affixed by a hook and loop, button and hook, or Velcro fastening system.

10. The adjustable arm sling of claim 1 further including a junction brace connecting the first and second straps along the hack of a patient wherein the straps form an x at the back of a patient.

11. A method of affixing an arm sling to a patient, the method comprising:
  providing an adjustable arm sling having a pouch and having straps extending from opposite ends of the pouch, each of the straps having at least one length adjusting device, the sling Further having a front brace and an elbowbrace, each having opposed ends affixed to the pouch;
  extending each of the straps over opposite shoulders of a patient and securing free ends of the straps to clothing of a patient along the patient's back,
  providing a length adjusting device on each strap located between the pouch and a shoulder of a patient; and
  adjusting the length of the straps by use of the length adjusting devices to position the pouch in a wrist up position to hold the arm of a patient
  extending the front brace across a hand of the patient and adjusting the hand brace to the hand to retain the hand securely to the arm sling;
  extending the rear brace across the arm of the patient and adjusting the elbow brace to the elbow to retain the elbow securely to the arm sling.

12. The method of claim 11 wherein the step of providing a sling having straps comprises providing an adjustable arm sling having straps having length adjusting devices located along the back of a patient when the adjustable arm sling is worn by a patient.

13. The method of claim 11 wherein the step of providing a sling comprises providing a sling having two length adjusting devices on each of the straps.

14. The method of claim 11 wherein the step of securing free ends of the straps comprises affixing the free ends to a belt or other clothing worn by a patient.

* * * * *